United States Patent [19]

Derreumaux et al.

[11] 4,278,507
[45] Jul. 14, 1981

[54] METHOD FOR AMPEROMETRIC MEASUREMENT OF THE FREE-CHLORINE CONTENT IN A SOLUTION

[76] Inventors: Antoine Derreumaux, 19, bd de Beauséjour, 75016 Paris; Bernard Saunier, 16, rue Gros Malhon, 35000 Rennes, both of France

[21] Appl. No.: 86,620

[22] Filed: Oct. 19, 1979

Related U.S. Application Data

[63] Continuation-in-part of Ser. No. 860,268, Dec. 13, 1977.

[51] Int. Cl.³ ........................................... G01N 27/46
[52] U.S. Cl. ............................... 204/1 T; 204/195 R; 23/230 R
[58] Field of Search ................... 204/1 BT, 195 R; 23/230 R, 230 B

[56] References Cited

U.S. PATENT DOCUMENTS

| | | | |
|---|---|---|---|
| 2,585,811 | 2/1952 | Marks | 204/195 R |
| 3,226,195 | 12/1965 | Nichols et al. | 23/230 R |
| 3,227,643 | 1/1966 | Okun et al. | 204/195 P |
| 3,413,199 | 11/1968 | Morrow | 23/230 R |
| 3,902,982 | 9/1975 | Nakagawa | 204/195 R |
| 3,921,439 | 11/1975 | Burns | 23/230 B |
| 3,923,460 | 12/1975 | Parrott et al. | 23/230 R |
| 3,959,087 | 5/1976 | Morrow | 204/195 R |
| 3,966,413 | 6/1976 | Marinenko | 23/230 R |
| 4,129,479 | 12/1978 | Morrow | 204/1 B |

OTHER PUBLICATIONS

Lambert et al., "Analytical Chemistry", vol. 41, No. 6, May 1969, pp. 838-840.
Zitomer et al., "Analytical Chemistry", vol. 34, No. 13, Dec. 1962, pp. 1738-1740.

Primary Examiner—T. Tung
Attorney, Agent, or Firm—William A. Drucker

[57] ABSTRACT

A method for measuring the free chlorine content in a solution consists, in first portions of the solution, in successively adding a chemical compound (e.g. a nitrite), which selectively transforms the free chlorine into chloride, then an iodide, in introducing the said first portions in an amperometric cell for measuring the combined chlorine content and, in second portions of the solution, in adding only the iodide and subsequently introducing the second portions into an amperometric cell for measuring the total chlorine content and finally in calculating the difference between the total chlorine and the combined chlorine contents.

5 Claims, 3 Drawing Figures

METHOD FOR AMPEROMETRIC MEASUREMENT OF THE FREE-CHLORINE CONTENT IN A SOLUTION

This application is a continuation-in-part of application Ser. No. 860,268, filed Dec. 13, 1977.

The invention concerns the chemical analysis of a solution containing chlorine in the form of "free chlorine" (HOCl and OCl$^-$) and in combined form, in particular chloramines.

Such an analysis is carried out in particular on water treated with chlorine for disinfection and sterilization. In the presence of ammonia and organic matter, chloramines form in proportions which are sometimes large and it is important to know accurately the residual free chlorine contents, which is much more active than chloramines.

A method currently used is amperometric analysis, carried out directly on the water, by means of electrodes one of which is, e.g., made of copper, the other of platinum, silver or carbon; the electrodes are subjected to a specific potential difference and immersed in the solution; a current is produced whose strength is in proportion to the chlorine concentration.

This method is applied to the determination of the total chlorine concentration. The addition of an iodide and a buffer at pH 4.0 before the passage between the two electrodes liberates the iodine with transformation of the various forms of chlorine into chloride. The diffusion current observed at the indicating electrode is a direct and accurate measurement of the iodine concentration, from which the chlorine content is deduced.

The instrument operates retaining its calibration for several weeks or even several months, no polarization film forming on the electrodes.

If it is wished to determine the free chlorine content, a direct amperometric analysis must be made, without using an iodide as a reagent and without buffering, so that only free chlorine is involved in the formation of the diffusion current.

Unfortunately, it is found that the presence of chloramines, even at low rates, gives assay results with an excess error, which is explained by the fact that some discharge of chlorine ions occurs from the chloramines. Moreover, a polarization film forms on the surface of the electrodes, which upsets its calibration of the instrument.

At present, therefore, there is no means of making a continuous, accurate and reliable amperometric analysis of the free chlorine contents in water containing chloramines, especially when the content of the latter is high.

The subject matter of the invention is a simple method making it possible to carry out such an analysis.

The method according to the invention comprises the amperometric analysis of the total chlorine using an iodide and possibly a buffer of pH 4.0 as reagents and is characterized by an additional amperometric analysis, carried out using an iodide and possibly a buffer at pH as reagents, on a solution previously treated with a chemical compound reacting selectively on the free chlorine.

The additional analysis measures the combined chlorine concentration, particularly as chloramines, and the free chlorine content is calculated by difference between the total chlorine and combined chlorine contents.

A further subject matter of the invention is an amperometric measuring instrument which applies the above method and includes means of carrying out the two analyses in parallel and means of calculating the difference between their results to obtain a direct indication of the free chlorine content.

Other peculiarities, as well as the advantages of the invention will emerge clearly from the following description of an example of implementation of the method.

This example is described with reference to the attached drawings, in which

Figures 1, 2, 3:
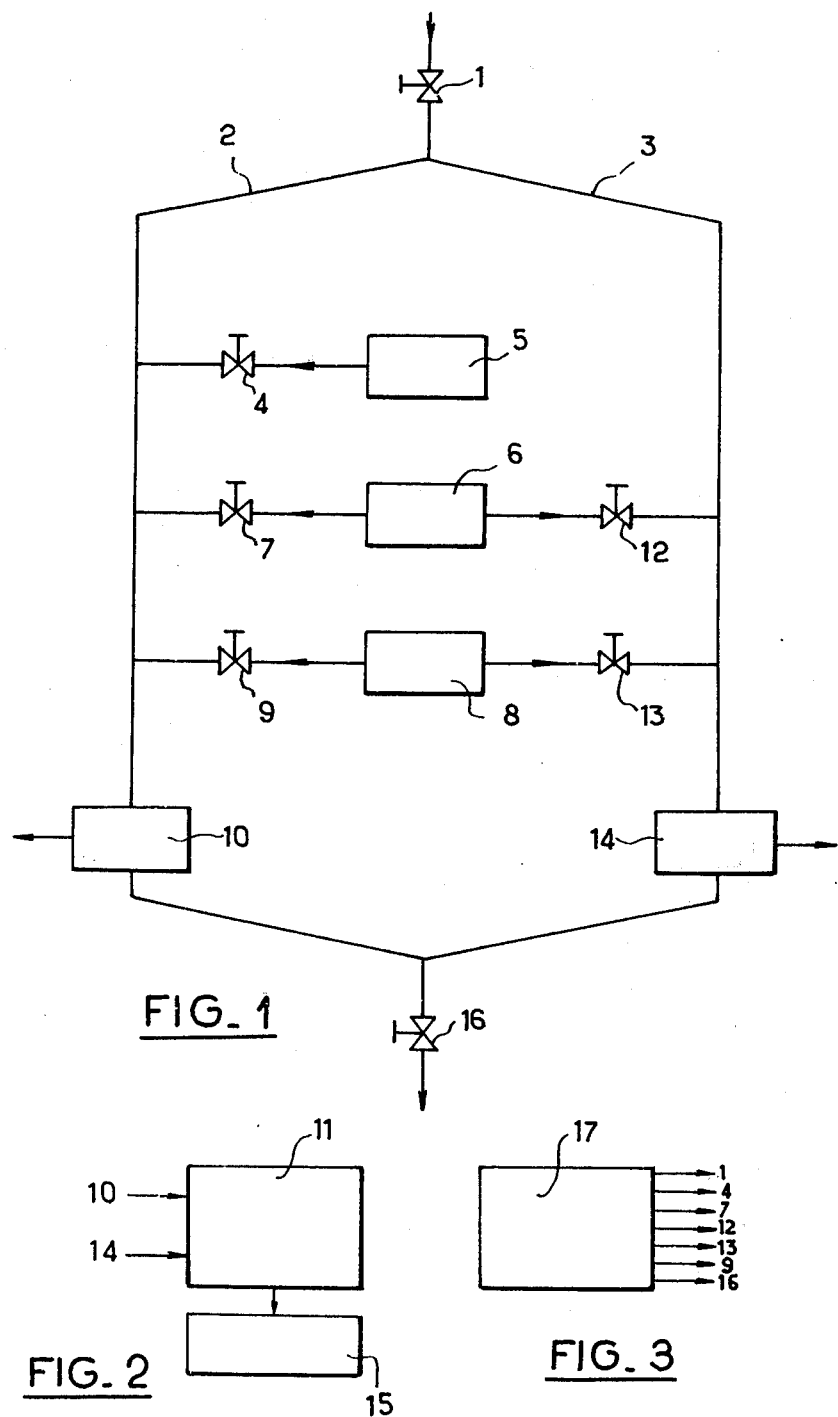
FIG. 1 is a partial diagram of an instrument in accordance with the invention.
FIG. 2 illustrates the calculating unit and display unit.
FIG. 3 illustrates the timer which is part of said instrument.

The instrument includes an electromagnetic sluice gate 1 which controls the intake of water for analysis to two pipes 2 and 3.

In pipe 2, the water first receives, through a regulating electromagnetic sluice gate 4, a nitrite, for example sodium nitrite, contained in a container 5.

The nitrite transforms the free chlorine into chloride by the reaction:

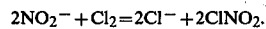

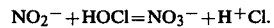

On the other hand, it virually does not react with the chloramines. The chlorine content in the chloramines is then measured. For this purpose, the solution is possibly buffered to pH 4.0 by adding a solution of acetic acid and acetate contained in a container 6, regulation being carried out by means of an electromagnetic sluice gate 7. Potassium iodide contained in container 8 is then introduced by means of regulating electromagnetic sluice gate 9. The measurement is carried out by means of a standard amperometric cell 10 which supplies a current $I_1$ to an electronic calculating device 11.

It has been found that introducing nitrite, (for example sodium nitrite) in excess as a reducing compound liquid carrying out the additional amperometric analysis so as to measure the combined chlorine, would normally cause detrimental drifting of the cell. This is probably due to physio-chemical reactions between the electrodes, a phenomenon which is not well understood.

However, the applicants have discovered that although this drifting effectively takes place with most amperometric analyzers, such drifting can be avoided by using a copper-gold couple of electrodes. The applicants also have discovered that, for any other electrode couple, such drifting can be avoided by further adding to the solution, before carrying out the additional amperometric analysis so as to measure the combined chlorine, ethylenediamine tetraacetic acid with a concentration of about 1 to 100 mg. per liter and preferably of about 5-10 mg. per liter.

In pipe 3, the total chlorine content in the water is analysed direct by the standard method.

The possibile buffer is injected through an electromagnetic sluice gate 12, the potassium iodide through an electromagnetic sluice gate 13 and the measurement is carried out by means of an amperometric cell 14, which supplies a current $I_2$ to device 11. The latter, from the value of $I_1$ and $I_2$, calculates the difference (proportional to $I_2-I_1$) between the total chlorine and combined chlorine contents, i.e. the free chlorine content. Digital or analog display or recording of the result is effected at 15.

The two pipes end at the drain, through an electromagnetic sluice gate 16.

In some applications, e.g. for analyzing the water in a swimming pool, since the concentrations evolve slowly, it is useful, in order to reduce reagent consumption, to operate the instrument intermittently only. For this purpose, the instrument comprises a timer 17, which controls the opening of the electromagnetic sluice gates for, e.g., one minute every two to five minutes.

The content measured just before a period when the electromagnetic sluice gates are open continues to be displayed during the ensuing closed period. At the next open period, a further measurement is made. Ten to thirty seconds are needed, at each opening, to stabilize the system. During this time, the measurements are not taken into account, the content measured just before the preceding closure continuing to be displayed or recorded.

Other chemical compounds which reset selectively on free chlorine can be used and, in particular, cyanates or phenols, at the rate of 5 to 2000 mg per liter of water to be analyzed and preferably of the order of 50 mg/l.

The table below allows a comparison to be made of results of analyses made with diethyl-p-phenylene diamine (DPD), by means of a standard analyzer and by means of the analyzer described above, respectively. The chlorine contents are indicated in mg/l. The DPD measurement serves as a control. It can be seen that, in experiments 1 and 2, in the presence of chloramine contents 7 to 15 times higher than the free chlorine content, the standard-type analyzer responds mainly to the combined chlorine, whereas the analyzer described indicates the free chlorine content with perfectly acceptable accuracy.

TABLE

|  | DPD | | Standard Analyzer | | Analyzer Described | |
| --- | --- | --- | --- | --- | --- | --- |
|  | Free $Cl_2$ | Total $Cl_2$ | Free $Cl_2$ | Total $Cl_2$ | Free $Cl_2$ | Total $Cl_2$ |
| Experiment 1 | 0.5 | 4.0 | 2.0 | 3.6 | 0.3 | 3.6 |
| Experiment 2 | 0.2 | 3.2 | 1.5 | 3.3 | 0.3 | 3.3 |
| Experiment 3 | 1.0 | 2.5 | 1.4 | 2.4 | 1.1 | 2.4 |
| Experiment 4 | 2.4 | 2.9 | 2.5 | 2.8 | 2.4 | 2.8 |

What is claimed is:

1. Method of measuring the free chlorine content in a solution containing chlorine both in free and combined form, comprising the steps of adding an amount of water-soluble iodide to a portion of the said solution to establish in said portion an iodine concentration stoichiometrically equivalent to the amount of total chlorine within said portion; of subsequently introducing said portion between the electrodes of amperometric detecting cell means; of measuring a first current flow through said amperometric detecting cell means as indicative of the total chlorine concentration in the solution; of adding to a further portion of the said solution a nitrite which reacts selectively with free chlorine to transform it into a chloride; of subsequently adding to said further portion an amount of water-soluble iodide to establish in said further portion an iodine concentration which is stoichiometrically equivalent to the amount of combined chlorine within said further portion; of subsequently introducing said further portion between the electrodes of amperometric detecting cell means; of measuring a second current flow through amperometric detecting cell means provided with one copper and one gold electrodes respectively, as indicative of the combined chlorine concentration in the solution; and of obtaining the difference between the said first and second current flows as indicative of the free chlorine concentration in the solution.

2. A method of measuring the combined chlorine content in a solution containing chlorine both in free and combined form, comprising the steps of adding to a portion of the said solution a nitrite which reacts selectively with free chlorine to transform it into a chloride; of subsequently adding to said portion an iodide to establish an iodine concentration which is stoichiometrically equivalent to the amount of combined chlorine within said portion; of subsequently introducing said portion between one copper and one gold electrodes of amperometric detecting cell means; and of measuring the current flow through said amperometric detecting cell means as indicative of the combined chlorine concentration in the solution.

3. Method of measuring the free chlorine content in a solution containing chlorine both in free and combined form, comprising the steps of adding an amount of water-soluble iodide to a portion of the said solution to establish in said portion an iodine concentration stoichiometrically equivalent to the amount of total chlorine within said portion; of subsequently introducing said portion between the electrodes of amperometric detecting cell means; of measuring a first current flow through said amperometric detecting cell means as indicative of the total chlorine concentration in the solution; of adding to a further portion of the said solution a chemical compound which reacts selectively with free chlorine to transform it into a chloride; of subsequently adding to said further portion an amount of water-soluble iodide to establish in said further portion an iodine concentration which is stoichiometrically equivalent to the amount of combined chlorine within said further portion and an additional amount of ethylenediamine tetraacetic acid in the range of about 1-100 mg per liter; of subsequently introducing said further portion between the electrodes of amperometric detecting cell means; of measuring a second current flow through said amperometric detecting cell means, as indicative of the combined chlorine concentration in the solution; and of obtaining the difference between the said first and second current flows as indicative of the free chlorine concentration in the solution.

4. A method of measuring the combined chlorine content in a solution containing chlorine both in free and combined form, in particular chloramines, comprising the steps of adding to a portion of the said solution a chemical compound which reacts selectively with free chlorine to transform it into a chloride; of subsequently adding to said portion an amount of water-soluble iodide to establish in said portion an iodine concentration which is stoichiometrically equivalent to the amount of combined chlorine within said portion and an additional amount of ethylenediamine tetraacetic acid in the range of about 1-100 mg per liter; of subsequently introducing said portion between the electrodes of amperometric detecting cell means; and of measuring the current flow through said amperometric detecting cell means as indicative of the combined chlorine concentrations in the solution.

5. A method according to claim 4 wherein the additional amount is in the range of 5-100 mg per liter.

* * * * *